(12) United States Patent
Hofmann et al.

(10) Patent No.: US 8,123,921 B2
(45) Date of Patent: Feb. 28, 2012

(54) METHOD AND DEVICE FOR THE PREPARATION OF LIQUID SAMPLES IN NMR SPECTROSCOPY USING A COMBINED TITRATION AND PH ELECTRODE

(75) Inventors: Gudrun Hofmann, Rheinstetten (DE); Martin Hofmann, Rheinstetten (DE)

(73) Assignee: Bruker BioSpin GmbH, Rheinstetten (DE)

(*) Notice: Subject to any disclaimer, the term of this patent is extended or adjusted under 35 U.S.C. 154(b) by 113 days.

(21) Appl. No.: 12/801,298

(22) Filed: Jun. 2, 2010

(65) Prior Publication Data
US 2010/0236943 A1    Sep. 23, 2010

Related U.S. Application Data

(63) Continuation of application No. 11/637,877, filed on Dec. 13, 2006, now abandoned.

(30) Foreign Application Priority Data

Dec. 20, 2005 (DE) .......... 10 2005 060 866

(51) Int. Cl.
*G01N 27/333* (2006.01)

(52) U.S. Cl. .......... 204/405; 205/787.5; 436/51

(58) Field of Classification Search .......... 204/405, 204/416, 420, 433, 435; 205/787.5; 422/12, 422/82.03; 324/437, 438, 439; 436/43, 51
See application file for complete search history.

(56) References Cited

U.S. PATENT DOCUMENTS

| | | | |
|---|---|---|---|
| 5,213,668 A * | 5/1993 | Zboril .......... | 205/787.5 |
| 6,926,814 B2 * | 8/2005 | Koenemann et al. .......... | 204/409 |

* cited by examiner

*Primary Examiner* — Alex Noguerola
*Assistant Examiner* — Gurpreet Kaur
(74) *Attorney, Agent, or Firm* — Paul Vincent

(57) ABSTRACT

A method and device have an electrode rod (1; 21) for a pH meter. The electrode rod (1; 21) has a measuring end (2; 22) for immersion into a liquid test sample (31), wherein the measuring end (2; 22) has a pH measuring element, and wherein electrical feed lines (5) in the electrode rod (1; 21) extend towards the pH measuring element. A plurality of capillaries (8, 9, 10; 23) for feeding liquids and gas into the test sample (31) extend in the electrode rod (1; 21) and have outlet openings (11, 12, 13; 24) in the area of the measuring end (2; 22). The method and device facilitate and accelerate preparation of liquid test samples and adjustment of a pH value for small amounts of test samples or narrow sample containers in NMR spectroscopy applications.

15 Claims, 4 Drawing Sheets

METHOD AND DEVICE FOR THE PREPARATION OF LIQUID SAMPLES IN NMR SPECTROSCOPY USING A COMBINED TITRATION AND PH ELECTRODE

This application is a continuation of Ser. No. 11/637,877 filed Dec. 13, 2006 now abandoned and also claims Paris Convention priority of DE 10 2005 060 866.3 filed Dec. 20, 2005 the complete disclosures of which are hereby incorporated by reference.

BACKGROUND OF THE INVENTION

The invention concerns a method and device using an electrode rod for a pH meter with a measuring end for immersion into a liquid test sample, wherein the measuring end comprises a pH measuring element and electrical feed lines in the electrode rod extend towards the pH measuring element.

An electrode rod of this type is disclosed e.g. in "IQ 240 Benchtop/Portable pH Meter" by I.Q. Scientific Instruments, Inc., San Diego, Calif., USA, 2001.

When substances, e.g. proteins, are measured using modern methods of instrumental analytics, the measuring result is not only influenced by the substance itself but also by the measuring surroundings. In particular, in NMR spectroscopy of substances in aqueous solution, the pH value considerably affects the obtained spectra.

A correlation between the measuring result and the measuring surroundings is sometimes possible, i.e. the influence of the measuring surroundings can be extracted from the measuring result, thereby obtaining information about the actual substance. It is generally simpler and more accurate to examine the substance in certain, defined measuring surroundings. Towards this end, the measuring surroundings of the substance must be adjusted before the measurement.

Solutions are particularly suited as measuring surroundings, since the substance is homogeneously distributed therein and the amount of a liquid test sample (that is the substance in a solution in the measuring surroundings) can be easily adjusted.

As a first step, adjustment of the measuring surroundings often includes adding a certain amount of a standard solution and/or a buffer solution. In a further step, the pH value is in general iteratively adjusted, typically to pH 7.0.

When a sufficient amount of the substance and therefore also of the liquid test sample is available, the test sample is disposed into a large sample container, e.g. a beaker in order to adjust the pH value. An electrode rod of a pH meter and two pipettes for adding acid and base are immersed into the test sample. Acid or base is added until a desired pH value is obtained, which is simultaneously measured by the pH meter. This method is illustrated e.g. in the company leaflet "Basic Titrino 794" by Metrohm Ionenanalytik.

In many applications of instrumental analytics, only small amounts of the substance to be measured are available and hence also of the liquid test sample, since the substance may generally not be excessively diluted before measurement in order to produce exact measuring results. Typical amounts of test sample for the analysis of mouse urine using NMR spectroscopy are e.g. 0.5 to 2 ml. The liquid test sample, whose pH value is to be adjusted, is thereby provided in a small and narrow sample container.

In this case, iterative adjustment of the pH value in accordance with prior art is very difficult. An electrode rod of a pH meter is initially immersed into the narrow sample container holding the test sample, and the pH value is determined. The electrode rod is then pulled out and a small amount of acid or base is added to the test sample. The test sample is briefly mixed and the electrode rod is subsequently immersed again to check the pH value. The electrode rod is removed again and acid or base is added in the required amounts. This is continued until the desired pH value is reached.

Due to the narrow sample container (e.g. a 2 ml glass vial with an opening width of approximately 5 mm), the electrode rod (smallest available outer diameter 3.8 mm) cannot remain in the sample container during titration of acid or base, since there is not enough space for pipettes.

For this reason, the laboratory equipment (electrode rod, mixer, acid pipette, base pipette) must be removed and reinserted from above the test sample a plurality of times during preparation of a small amount of liquid test sample, which renders preparation of such a test sample very time-consuming and therefore expensive.

It is therefore the underlying purpose of the present invention to facilitate and accelerate preparation of liquid test samples, in particular adjustment of the pH value, for small amounts of test sample and in narrow sample containers. Automation of the preparation of the liquid test samples should also be simplified.

SUMMARY OF THE INVENTION

This object is achieved with a method for preparing a liquid sample for NMR spectroscopy using a combined titration and pH electrode having an electrode rod for a pH meter, the method comprising the steps of:

a) positioning the electrode rod in a substantially vertical orientation with a measuring end thereof facing downwardly, the electrode rod measuring end being structured for immersion into the liquid sample, wherein the electrode rod comprises a pH measuring element disposed in the measuring end, electrical feed lines extending in the electrode rod to the pH measuring element, an acid capillary extending within the electrode rod for feeding an acidic fluid into the liquid sample, the acid capillary having an acid outlet opening in a bottom of the measuring end, a base capillary extending within the electrode rod for feeding a basic fluid into the liquid sample, the base capillary having a base outlet opening in the bottom of the measuring end, and a gas capillary extending within the electrode rod for feeding a gas into the liquid sample, the gas capillary having a gas outlet opening in the bottom of the measuring end;

b) immersing the measuring end into the liquid sample following step a);

c) discharging gas out of the gas opening following step b);

d) measuring a pH value of the liquid sample following or during step c);

e) if results of step d) indicate a measured pH value which exceeds a desired pH value, discharging acid out of the acid opening;

f) if results of step d) indicate a measured pH value which is less than a desired pH value, discharging base out of the base opening;

g) repeating steps c) through f) with the measuring end remaining immersed in the liquid sample until the measured pH value substantially equals the desired pH value.

The object of the invention is also achieved with a device specially structured to carry out the inventive method.

The inventive method and device permits maintenance of the electrode rod immersed in a sample container in a test sample and at the same time direct supply of a fluid, in particular, acid or base to the test sample through the capillary of the electrode rod. Even when the test sample is kept in a narrow container, the electrode rod need not be removed in order to titrate the fluid. With the inventive method and device, the laboratory equipment need not be moved relative to the sample container during sample preparation between pH measurement and titration. This facilitates and accelerates iterative adjustment of the pH value of a test sample.

Automatic sample preparation only requires one single movement of one single piece of laboratory equipment, i.e. the inventive electrode rod, over the sample container and immerse it into the test sample. The whole sample preparation, in particular, complete titration may be performed while the inventive electrode rod is immersed.

The electrode rod may subsequently be removed and (following cleaning) be used in a further test sample in another sample container. This facilitates automatic sample preparation.

The fact that the electrode rod must be immersed only once for preparing the sample also reduces the danger of soiling the test sample.

In a particularly preferred embodiment of the inventive electrode rod, several, preferably 2, 3 or 4 capillaries are provided in the electrode rod each having one outlet opening in the area of the measuring end. The plurality of capillaries provides the inventive electrode rod with a multitude of functions and saves further operations for sample preparation. The capillaries are provided, in particular, for acid, base, gas and buffer and/or standard solution. Acid thereby means a solution having a smaller pH value than the test sample, and a base means a solution having a higher pH value than the test sample. The acid and base capillaries may also correct the pH value when the target value has been overshot. The buffer/standard solution capillary saves one further sample preparation step. The gas capillary permits faster, more thorough and simpler mixing of the test sample.

In another preferred embodiment, the capillary/capillaries is/are produced from glass, in particular, quartz glass of high purity ("fused silica") or of metal, in particular, stainless steel or plastic material, in particular PTFE (polytetrafuoroethylene) or PEEK (polyetheretherketone). These materials are advantageous due to their chemical resistance, and special steel and plastic materials are also advantageous due to their mechanical stability.

In another preferred embodiment, the pH measuring element has a sensor chip and a reference electrode, wherein the sensor chip is preferably designed as an ISFET (ion sensitive field effect transistor). This design of the sensor chip has proven to be practical.

In one further preferred embodiment of the inventive electrode rod, a temperature sensor is provided in the area of the measuring end.

In another embodiment, the electrode rod has an outer diameter of between 2 mm and 7 mm in the area of the measuring end. These values are particularly suited for handling sample containers for small amounts of test sample in the range between 0.5 and 2 ml.

In another advantageous embodiment, the capillary/capillaries has/have an inner diameter of between 50 μm and 500 μm. These diameters are also adjusted for small amounts of test samples.

One embodiment of the inventive electrode rod is particularly preferred with which the measuring end tapers in a pointed or beveled fashion. Such a measuring end is suited to penetrate through an upper sealing of a sample container, i.e. a plastic diaphragm. No separate operation is required for opening a sample container.

In an advantageous embodiment, the outlet opening of a lower capillary is closer to the end of the electrode rod than the pH measuring element. This lower capillary is mainly suited as a gas capillary. In an upright position of the electrode rod, i.e. the measuring end faces downwards and is immersed into the test sample, gas that rises from the outlet opening of the lower capillary can be mixed with the test sample in the area around the pH measuring element. This makes the pH measurement more reliable.

In a preferred further development of this embodiment, the outlet openings of the other capillaries are further away from the end of the electrode rod than the outlet opening of the lower capillary. This also allows mixing through rising gas at the outlet openings of the other capillaries (i.e. acid and base capillaries) to accelerate titration.

The invention therefore concerns a method and device having an electrode rod for adjusting the pH value of a liquid test sample, wherein a titration liquid is supplied through the at least one capillary. Change between titration and pH measurement is possible without withdrawing the electrode rod. This facilitates and accelerates adjustment of the pH value of the test sample.

In a preferred variant of the inventive method, an acid is supplied through a first capillary and a base is supplied through a second capillary. This permits correction of the pH value when the target value has been overshot (e.g. on the acid side). This is particularly useful when the acid or base is present in a relatively high concentration such that excess amounts can occur.

In a further preferred variant of the method, a gas, in particular, an inert gas such as nitrogen, a rare gas or air is supplied through a third capillary, in particular, the lower capillary. The gas is mixed with the test sample in a simple and reliable fashion, thereby accelerating adjustment of the balanced conditions.

In another preferred variant of the method, a buffer solution is supplied via a fourth capillary. The buffer solution need not be supplied in a separate operation.

The present invention also concerns a titration unit comprising an inventive electrode rod with at least two capillaries in the electrode rod, a pH meter which is connected to the pH measuring element, an acid reservoir and a base reservoir, two pumps which may supply acid or base through one respective capillary, and a control means which is designed to drive the pumps such that defined amounts of acid or base are supplied to the outlet openings. The titration unit facilitates sample preparation of a liquid test sample, in particular, adjustment of the pH value, wherein the electrode rod may remain in the sample container during the entire sample preparation, even when it is narrow.

In a particularly preferred embodiment of the inventive titration unit, the control unit is moreover designed to adjust the pH value of a liquid test sample in an automatic, iterative fashion. This embodiment minimizes the number of staff required for sample preparation. The amount of acid or base that is supplied in one titration step is preferably reduced when the difference between the instantaneous pH value and the target pH value decreases.

In another preferred embodiment, the titration unit also comprises a gas pump, which may supply gas through a third, in particular, the lower capillary, and the control unit is designed to drive the gas pump, such that gas may also be supplied during and/or after supplying acid and/or base. This provides thorough mixing of the test sample and a balanced pH value is reached more quickly.

In another preferred embodiment, the titration unit also comprises a buffer reservoir and a buffer pump, which can supply the buffer solution from the buffer reservoir through a fourth capillary. With this titration unit, no separate operation for supplying buffer solution is required. The buffer solution may also be contained in or replaced by a standard solution for physical measurement of the test sample.

Further advantages of the invention can be extracted from the description and the drawing. The embodiments mentioned above and below may be used in accordance with the invention either individually or collectively in arbitrary combination. The embodiments shown and described are not to be understood as exhaustive enumerations, rather have exemplary character for illustrating the invention.

The invention is shown in the drawing and explained in more detail with reference to embodiments.

BRIEF DESCRIPTION OF THE DRAWING

FIG. 1b shows a schematic view on the measuring end of the electrode rod of FIG. 1a;

FIG. 2b shows a schematic view of the measuring end of the electrode rod of FIG. 2a;

DESCRIPTION OF THE PREFERRED EMBODIMENT

The present invention provides an electrode rod for a pH meter for measuring the pH value of a surrounding liquid test sample, as well as adding at least one titration liquid to the test sample through at least one capillary (a thin tube) which is provided in the electrode rod. The electrode may remain in the sample container, being immersed in the test sample during the entire sample preparation of repeated, alternating pH measurements and addition of fluid. An associated sample container, which contains the test sample and into which the inventive electrode rod is immersed requires only one opening width, which corresponds to the outer cross-sectional dimensions of the electrode rod in the area of its measuring end. In particular, no space is required for separate titration pipettes. The inventive measuring electrode is therefore particularly suited for preparing small amounts of test sample which are required e.g. in NMR spectroscopy of body liquid samples (urine, blood and the like). These small amounts of test sample are stored in small sample containers, which provide a volume into which a pH measuring element can be immersed.

Figure 1A:
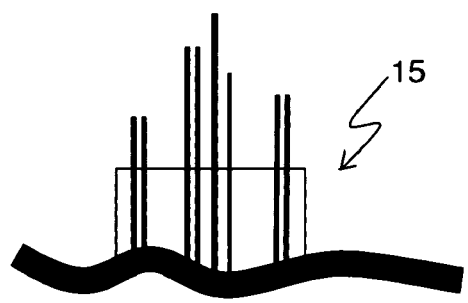
FIG. 1a shows a schematic cross-sectional view of an embodiment of an inventive electrode rod with three capillaries.
Figure 1A:
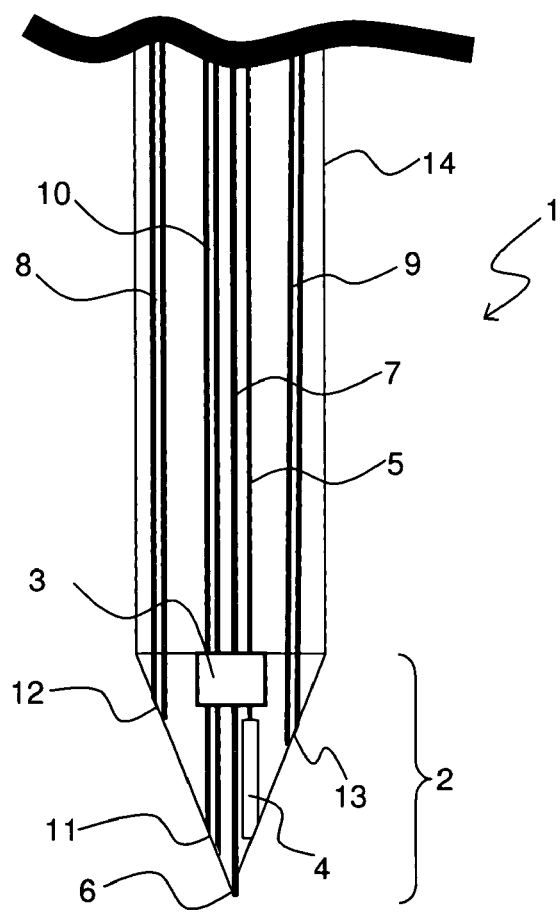

FIG. 1a shows a first embodiment of an inventive electrode rod 1. The electrode rod 1 is substantially circular cylindrical. The electrode rod 1 is not shown in its full length for reasons of simplification. A pH measuring element is provided at one measuring end 2, which tapers like a cone and comprises a sensor chip 3 and a reference electrode 4. Electrical feed lines 5 inside the electrode rod 1 extend to the sensor chip 3 and the reference electrode 4. A temperature sensor 6 is provided at the lower tip of the measuring end 2, which also has an electric feed line 7.

In the embodiment of FIG. 1a, three capillaries 8, 9, 10, extend inside the electrode rod. A capillary 8 for an acid and a capillary 9 for a base are disposed on opposing sides in the electrode rod 1, close to the outer sleeve of the electrode rod 1. This is intended to prevent neutralization of acid and base in the capillaries 8, 9 through diffusion. A third capillary 10 is provided for nitrogen gas. An outlet opening 11 of the third capillary 10 is quite close to the tip of the measuring end 2. When the electrode rod 1 is in an upright position which is the typical position of use of the electrode rod (with the measuring end 2 facing vertically downwards), this outlet opening 11 is below the outlet openings 12, 13 of the capillaries 8, 9 for acid and base and also below the sensor chip 3, which is a substantial part of the pH measuring element. When gas bubbles exit the outlet opening 11, they whirl the liquid test sample above them, in particular in front of the other outlet openings 12, 13 and the sensor chip 3.

The electrode rod 1 has a cladding 14 of special steel, which provides the electrode rod 1 with sufficient stability for daily use and, in particular, renders it unbreakable. The capillaries 8, 9, 10 are produced from quartz glass of high purity and have e.g. an outer diameter of 360 μm and an inner diameter of 220 μm. For typical titration, the acid and base should cover an operating range of at least pH 4.01 to pH 7.00. In accordance therewith, the acid in capillary 8 has a pH value of less than 4.01 and the base in capillary 9 has a pH value of more than 7.00.

The overall electrode rod 1 is mounted to a robot arm which can be preferably moved in all spatial directions X, Y, Z (not shown). The electrode rod 1 may thereby be automatically moved between the different positions of sample containers to thereby test samples. A further robot arm may be provided for moving sample containers (not shown).

A connection, e.g. a plug connection, to a flexible line (not shown) is provided at the upper end 15 of the electrode rod 1. The flexible line contains cables and hoses e.g. PTFE hoses in order to connect the electrical feed lines 5, 7 and the capillaries 8, 9, 10 to a control means.

Figure 1B:
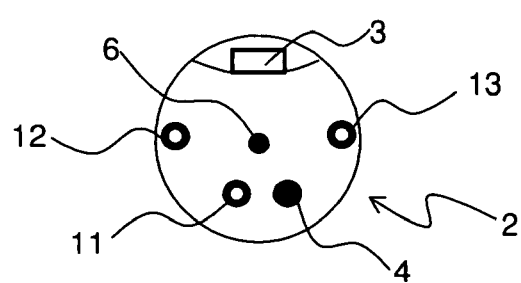

FIG. 1b shows a view from below of the measuring end 2 of the electrode rod of FIG. 1a. The outlet openings 12, 13 of the capillaries of acid and base have a maximum separation. The cross-section of the electrode rod is circular.

Figure 2A:
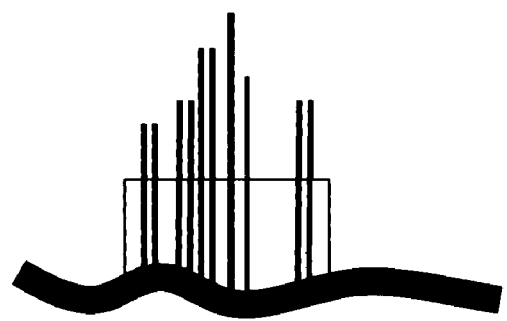
FIG. 2a shows a schematic cross-sectional view of an embodiment of an inventive electrode rod with four capillaries.
Figure 2A:
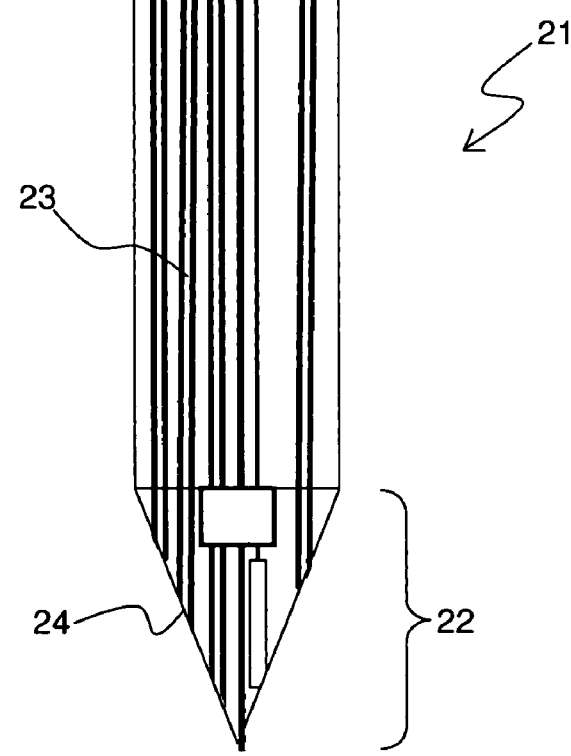
Figure 2B:
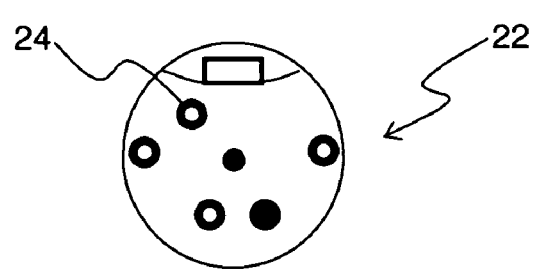

FIGS. 2a and 2b show an embodiment of an electrode rod 21 and its measuring end 22 similar to FIGS. 1a, 1b. The electrode rod 21 has a further, fourth capillary 23 with an outlet opening 24 through which the buffer solution can be introduced into a test sample. For this reason, the buffer solution, which is typically supplied before the pH value, is adjusted in highly acidic or highly basic test samples (the buffer capacity of the supplied buffer solution is thereby exhausted) need not be supplied in a separate step but may also be supplied via the electrode rod 21.

Figure 3:
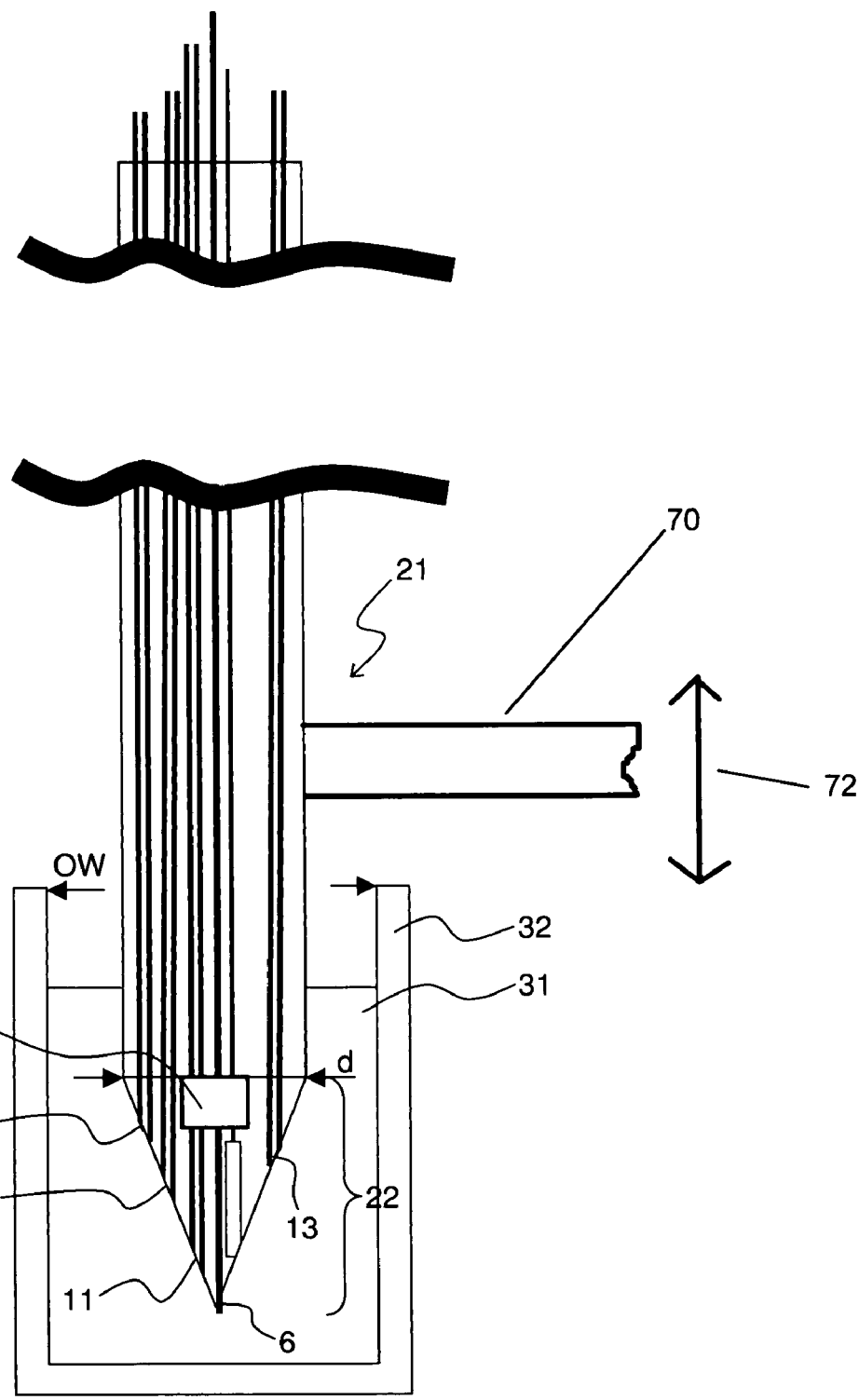
FIG. 3 shows a schematic view of the electrode rod of FIG. 2a, which is immersed into a test sample in a sample container.

FIG. 3 shows the electrode rod 21 of FIG. 2a, which is immersed into a liquid test sample 31. The test sample 31 is contained in a sample container 32. The electrode rod 21 is immersed into the test sample 31 until the entire measuring end 22, in particular, all outlet openings 11, 12, 13, 24, the temperature sensor 6 and the sensor chip 3 are surrounded by the liquid test sample 31.

The opening of the sample container 32 is only somewhat wider than the diameter of the electrode rod 21, such that the test sample 31 cannot be reached, or only with great difficulty, with a separate pipette when the electrode rod 21 is immersed. The largest outer diameter d of the electrode rod 21 in the area of the measuring end 22 is approximately 3.8 mm in the embodiment shown, and the diameter OW of the opening of the sample container 32 is approximately 5.0 mm. The sample container 32 may e.g. be an NMR sample tube. An appropriate mechanism 70 is provided for holding the electrode rod 21 and for vertical positioning thereof in the sample container 32 (indicated schematically with vertical double arrow 72)

Figure 4:
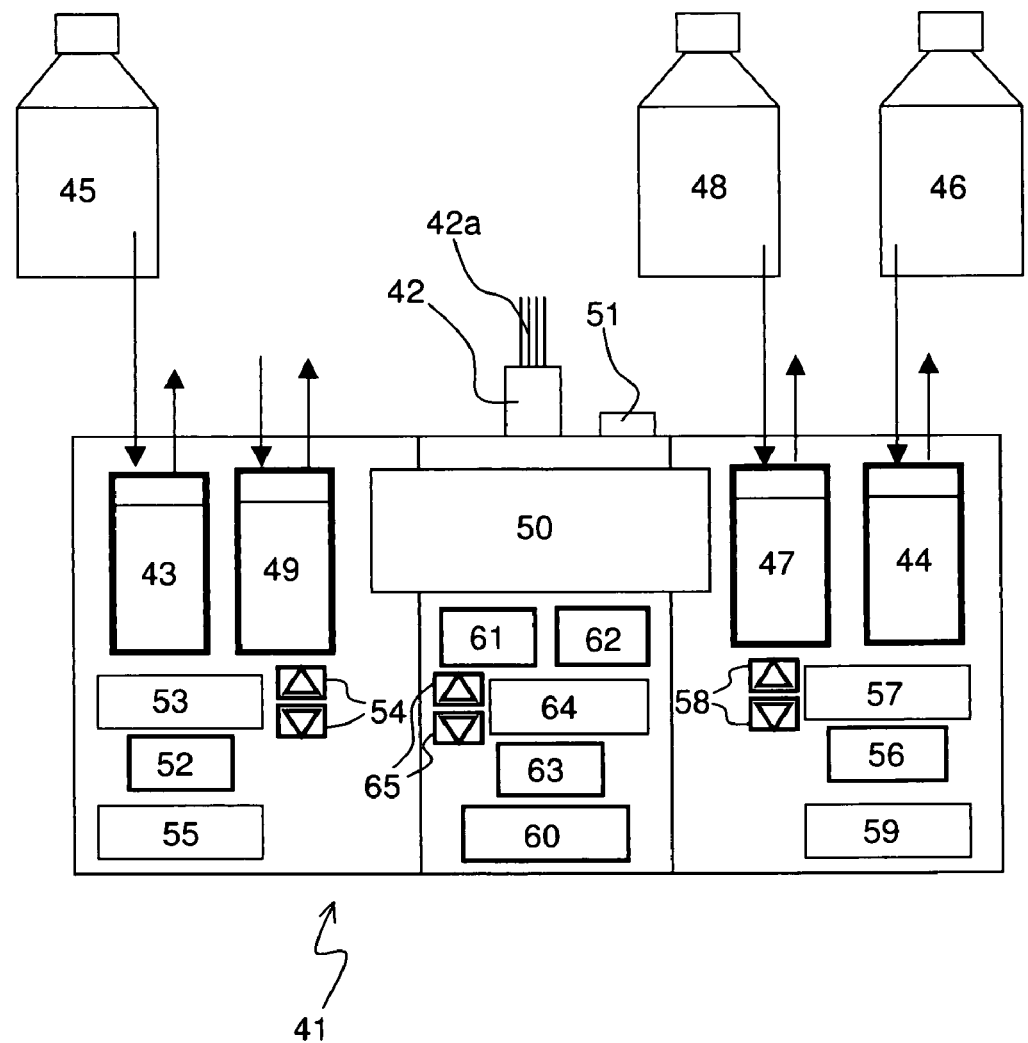
FIG. 4 shows a schematic view of a control means for an inventive titration unit.

FIG. 4 schematically shows a control means 41 for an inventive titration unit which comprises an electrode rod in accordance with FIGS. 2a, 2b.

The control means 41 has a plug connection 42 with a flexible line 42a, which is connected to the inventive electrode rod (not shown). A computer may be connected via a further plug connection 51 which may receive or pass on data from/to the control means 41.

Pumps 43, 44 for acid and base are provided in the control means 41, which can pump acid and base, respectively, from an acid reservoir 45 and a base reservoir 46 into the flexible line 42a and thereby into the electrode rod and the test sample. A buffer pump 47 may moreover pump a buffer solution from a buffer reservoir 48 into the flexible line 42a. The pumps 43, 44, 47 are designed as DNP gear pumps. A gas pump 49 may pump air from the surroundings into the flexible line 42a. The flexible line 42a has four PTFE hoses in order to separately guide the fluids.

The control means 41 receives information about the pH value and the temperature of the test sample via the plug connection 42 to the electrode rod. The pH value and the temperature are displayed on a display 50.

The control unit 41 provides for manual and also automatic titration.

During manual operation, acid can be supplied to the test sample via a key 52 "add". The amount of acid for each key depression is displayed on a display 53 "step size" and can be changed via the keys 54 "up/down". Typical acid volumes per titration step are in a range between 1 and 10 µl. The overall acid volume added during one titration is displayed on a display 55 "total vol.". Base may be supplied to the test sample via a key 56 "add". The amount of base for each key depression is displayed on a display 57 "step size" and may be changed via the keys 58 "up/down". Typical base volumes per titration step are also in a range between 1 and 10 µl. The overall volume of base added during one titration is displayed on a display 59 "total vol.". The gas pump 49 can be activated and deactivated via a key 60 "mix" such that the test sample is mixed. The key 61 "get pH" up-dates the pH measurement of the test sample. The pH meter of the titration means may also be calibrated via a key 62 "calibr. pH". Finally, buffer solution may be added to the test sample via a key 63 "add". The amount of buffer solution added per key depression is displayed on a display 64 and can be changed via keys 65.

Automatic operation is preferably effected via a computer, e.g. a PC, which is connected to the control, means 41 via the plug connection 51. Software is run on the PC which controls the added amounts of acid or base via control signals transmitted by the computer to the control means 41 on the basis of a predetermined target pH value in the computer and the read-out actual pH value. With decreasing difference between the predetermined and actual pH values, the acid or base is preferably added at a slower rate (i.e. the added amount per titration step decreases).

In another embodiment of the control unit 41, a target pH value may be predetermined at the control unit 41 itself, and automatic titration may be started via a further key. The control unit 41 itself then has sufficient computational resources.

Further functions may be provided on the control means 41 for automating sample preparation, in particular
  rinsing of the titration unit (in particular, pumps, hoses and capillaries) when the titration liquid is changed,
  setting of the mixing time;
  setting of the supply speed at the pumps;
  cleaning of the electrode rod;
  automatic calibration of the pH meter (in dependence on time or on the number of measurements).

We claim:

1. A method for preparing a liquid sample for NMR spectroscopy using a combined titration and pH electrode having an electrode rod for a pH meter, the method comprising the steps of:
   a) positioning the electrode rod in a substantially vertical orientation with a measuring end thereof facing downwardly, the electrode rod measuring end being structured for immersion into the liquid sample, wherein the electrode rod comprises a pH measuring element disposed in the measuring end, electrical feed lines extending in the electrode rod to the pH measuring element, an acid capillary extending within the electrode rod for feeding an acidic fluid into the liquid sample, the acid capillary having an acid outlet opening in a bottom of the measuring end, a base capillary extending within the electrode rod for feeding a basic fluid into the liquid sample, the base capillary having a base outlet opening in the bottom of the measuring end, and a gas capillary extending within the electrode rod for feeding a gas into the liquid sample, the gas capillary having a gas outlet opening in the bottom of the measuring end;
   b) immersing the measuring end into the liquid sample following step a);
   c) discharging gas out of the gas opening following step b);
   d) measuring a pH value of the liquid sample following or during step c);
   e) if results of step d) indicate a measured pH value which exceeds a desired pH value, discharging acid out of the acid opening;
   f) if results of step d) indicate a measured pH value which is less than a desired pH value, discharging base out of the base opening;
   g) repeating steps c) through f) with the measuring end remaining immersed in the liquid sample until the measured pH value substantially equals the desired pH value.

2. The method of claim 1, wherein a buffer solution is supplied through a fourth capillary.

3. A device for preparing a liquid sample for NMR spectroscopy using a combined titration and pH electrode having an electrode rod for a pH meter, the device comprising:
   a mechanism for positioning the electrode rod in a substantially vertical orientation with a measuring end thereof facing downwardly, the electrode rod measuring end being structured for immersion into the liquid sample, wherein the electrode rod comprises a pH measuring element disposed in the measuring end, electrical feed lines extending in the electrode rod to the pH measuring element, an acid capillary extending within the electrode rod for feeding an acidic fluid into the liquid sample, the acid capillary having an acid outlet opening in a bottom of the measuring end, a base capillary extending within the electrode rod for feeding a basic fluid into the liquid sample, the base capillary having a base outlet opening in the bottom of the measuring end, and a gas capillary extending within the electrode rod for feeding a gas into the liquid sample, the gas capillary having a gas outlet opening in the bottom of the measuring end;
   a mechanism for immersing the measuring end into the liquid sample;
   a mechanism for discharging gas out of the gas opening;

a mechanism for measuring a pH value of the liquid sample;

a mechanism for discharging acid out of the acid opening if a measured pH value exceeds a desired pH value;

a mechanism for discharging base out of the base opening if the measured pH value is less than a desired pH value; and a mechanism for cyclic adjustment of the pH value with the measuring end remaining immersed in the liquid sample until the measured pH value substantially equals the desired pH value.

4. The device of claim 3, wherein at least one of said acid, base and gas capillaries is made from glass, quartz glass of high purity, "fused silica", metal, stainless steel, plastic material, PTFE (polytetrafuoroethylene), or PEEK (polyetheretherketone).

5. The device of claim 3, wherein said pH measuring element has a sensor chip or an ISFET (ion sensitive field effect transistor) and a reference electrode.

6. The device of claim 3, further comprising a temperature sensor disposed in an area of said measuring end.

7. The device of claim 3, wherein said electrode rod has an outer diameter of between 2 mm and 7 mm in an area of said measuring end.

8. The device of claim 3, wherein said capillary has an inner diameter of between 50 μm and 500 μm.

9. The device of claim 3, wherein said measuring end is pointed or beveled.

10. The device of claim 3, wherein said gas opening is closer to an end of said electrode rod than said pH measuring element.

11. The device of claim 10, wherein said acid and base openings are further away from an end of said electrode rod than said gas opening.

12. A titration unit having the device of claim 3, the titration unit comprising:

a pH meter connected to said pH measuring unit;

an acid reservoir;

an acid pump connected to said acid reservoir to pass acid to one of said capillary outlet openings;

a base reservoir;

a base pump connected to said base reservoir to pass base to an other one of said capillary outlet openings; and a mechanism for controlling said acid pump and said base pump to supply defined amounts of acid and base to the sample.

13. The titration unit of claim 12, wherein said controlling means is designed to automatically, iteratively adjust a pH value of the liquid test sample.

14. The titration unit of claim 12, further comprising a gas pump to supply gas through a capillary or through a lower capillary, wherein said controlling means drives said gas pump in such a manner that gas can be supplied during and/or after supplying acid and/or base.

15. The titration unit of claim 12, further comprising a buffer reservoir and a buffer pump for supplying buffer solution from said buffer reservoir through a capillary.

* * * * *